US00PP32464P2

(12) United States Plant Patent
Smith et al.

(10) Patent No.: US PP32,464 P2
(45) Date of Patent: Nov. 17, 2020

(54) AVOCADO ROOTSTOCK NAMED 'MERENSKY 5'

(50) Latin Name: ***Persea americana* Mill**
Varietal Denomination: Merensky 5

(71) Applicants: Westfalia Fruit Estate Pty Ltd, Tzaneen (ZA); South African Avocado Growers Association, Tzaneen (ZA)

(72) Inventors: Duncan G. Smith, Somis, CA (US); Sylvie Kremer-Köhne, Haenertsburg (ZA); Zelda van Rooyen, Tzaneen (ZA); Josef Stefan Köhne, Tzaneen (ZA)

(73) Assignees: Westfalia Fruit Estate Pty Ltd, Tzaneen (ZA); South African Avocado Growers Association, Tzaneen (ZA)

( * ) Notice: Subject to any disclaimer, the term of this patent is extended or adjusted under 35 U.S.C. 154(b) by 0 days.

(21) Appl. No.: 16/602,695

(22) Filed: Nov. 20, 2019

(51) Int. Cl.
*A01H 5/08* (2018.01)
*A01H 6/52* (2018.01)

(52) U.S. Cl.
USPC ..... Plt./200

(58) Field of Classification Search
USPC ..... Plt./200
See application file for complete search history.

(56) References Cited

U.S. PATENT DOCUMENTS

| | | | |
|---|---|---|---|
| PP139 | P | 8/1935 | Hass |
| PP15,309 | P3 | 11/2004 | Köhne |
| PP17,947 | P3 | 8/2007 | Darvas |

*Primary Examiner* — Susan McCormick Ewoldt
(74) *Attorney, Agent, or Firm* — Kelly & Kelley, LLP

(57) ABSTRACT

A new avocado variety, 'Merensky 5' has high tolerance to salinity and to *Phytophthora cinnamomi* when used as a rootstock. 'Hass' trees grafted onto the 'Merensky 5' rootstock bear good yields.

6 Drawing Sheets

Latin name of the genus and species: *Persea americana* Mill.

Varietal denomination: 'Merensky 5'.

BACKGROUND OF THE INVENTION

The present invention is generally directed to a new avocado plant, or variety of *Persea americana* Mill. The varietal denomination of the avocado rootstock of the present application is 'Merensky 5'.

*Phytophthora* is a genus of plant-damaging oomycetes (water molds), capable of causing enormous economic losses on crops worldwide. *Phytophthora cinnamomi* is a soil-borne water mold that produces an infection which causes a condition in plants called "root rot" or "dieback". The plant pathogen is one of the world's most invasive species and is present in over seventy countries around the world. It is distributed worldwide and causes damage on hundreds of hosts. The disease affects a range of economic groups, such as food crops including avocados. It is a root pathogen that causes root rot and death of host plants. *Phytophthora cinnamomi* is the leading cause of damage to avocado trees amongst avocado farmers. Damaged trees generally die or become unproductive within three to five years. The discovery and utilization of avocado varieties, including rootstocks, which are resistant or have a tolerance to *Phytophthora cinnamomi* is highly desirable.

Growing avocado trees in areas which have high salinity also produces challenges and negative consequences to avocado farmers. The avocado tree is considered to be highly sensitive to salt, and particularly chloride ions. High salinity has been found to have a negative impact on the health of the avocado tree, as well as fruit yield, size and quality. It would be very desirable to avocado farmers to have avocado trees having a high tolerance to salinity.

Currently, the main avocado variety grown and consumed in the world is 'Hass' (U.S. Plant Pat. No. 139, the contents of which are incorporated herein by reference). The main markets have year-round supply of 'Hass' avocados and end consumers are very used to buying 'Hass'. Many other avocado varieties have been created and patented over the years, but none of them have been able to obtain important interest from growers, primarily due to the market still preferring the 'Hass' avocado fruit. It would be very desirable to be able to graft 'Hass' trees onto a rootstock which bear good yields.

SUMMARY OF THE INVENTION

In Tzaneen, Limpopo Province, South Africa, the yields of thousands of mature 'Fuerte' (not patented) avocado trees on seedling rootstocks of unknown parentage were evaluated in the late 1980s. Based on consistently high yields over a four-year period, top performing trees were identified. As high production potential may be due to the rootstock, the scion or the rootstock/scion combination, the rootstocks associated with high yields were obtained for further study.

Rootstock shoots were induced on these high-yielding trees and budwood was collected and then grafted to stumps of adult avocado trees in the orchard. The grafted budwood grew into trees which provided budwood for producing clonal trees, using the nurse seed/etiolation system, for further testing. These clonal trees were screened for their tolerance to root rot by exposure to a virulent strain of *Phytophthora cinnamomi* Rands in a mistbed, as root rot caused by this pathogen is an important disease of avocado.

After six weeks in the mistbed, the clonal trees were compared to 'Duke 7' (not patented). The clonal rootstocks found to be more tolerant to *Phytophthora cinnamomi* root rot than 'Duke 7' were selected and propagated for field trials.

The selected clonal rootstock 'Merensky 5' was developed, as described above, and subjected to various field trials under a range of growing conditions. The traits of 'Merensky 5' were found to be stable and progeny formed by asexual propagation true to type. While field testing of 'Merensky 5' did not prove the selection to be an improvement on 'Merensky 2' (U.S. Plant Pat. No. 15,309) in terms of *Phytophthora cinnamomi* tolerance, research trials conducted in Calif., USA, indicated that 'Merensky 5' offered salinity tolerance. The potential for salinity tolerance warranted further field testing of the rootstock under salinity conditions, which is a current challenge for avocado producers, such as those in Calif., USA.

'Merensky 5' is a new and distinct avocado variety, with the avocado rootstock thereof characterized by superior tolerance to saline conditions, as compared to 'Merensky 2'. 'Merensky 5' has also been found to have a high resistance or tolerance to *Phytophthora cinnamomi*. Moreover, 'Hass' grafted onto 'Merensky 5' bears more fruit than 'Hass' grown on 'Merensky 2'.

BRIEF DESCRIPTION OF THE DRAWINGS

The accompanying photographs show specimens of the tree and plant parts of the new 'Merensky 5' variety.

DETAILED BOTANICAL DESCRIPTION OF THE VARIETY

The following is a detailed description of the new 'Merensky 5' variety, which was taken from approximately 4-year-old mature trees, with the exception as a rootstock for a specific scion when reference is made to root rot and salt tolerance as well as yield. The trees are located in an experimental orchard at Tzaneen, Limpopo Province, South Africa, and are grafted on a 'Merensky 2' rootstock.

In those instances where precise color assessment could be made, The Royal Horticulture Society (R.H.S.) color numbering system (R.H.S. Colour Chart published by The Royal Horticultural Society, London 2001) is used herein for the color description of the rind, seed, bark, leaf, flower, flesh color and other characters of the 'Merensky 5' avocado tree. In other instances, generally, color terms are used in accordance with an ordinary dictionary significance.

Figure 1:
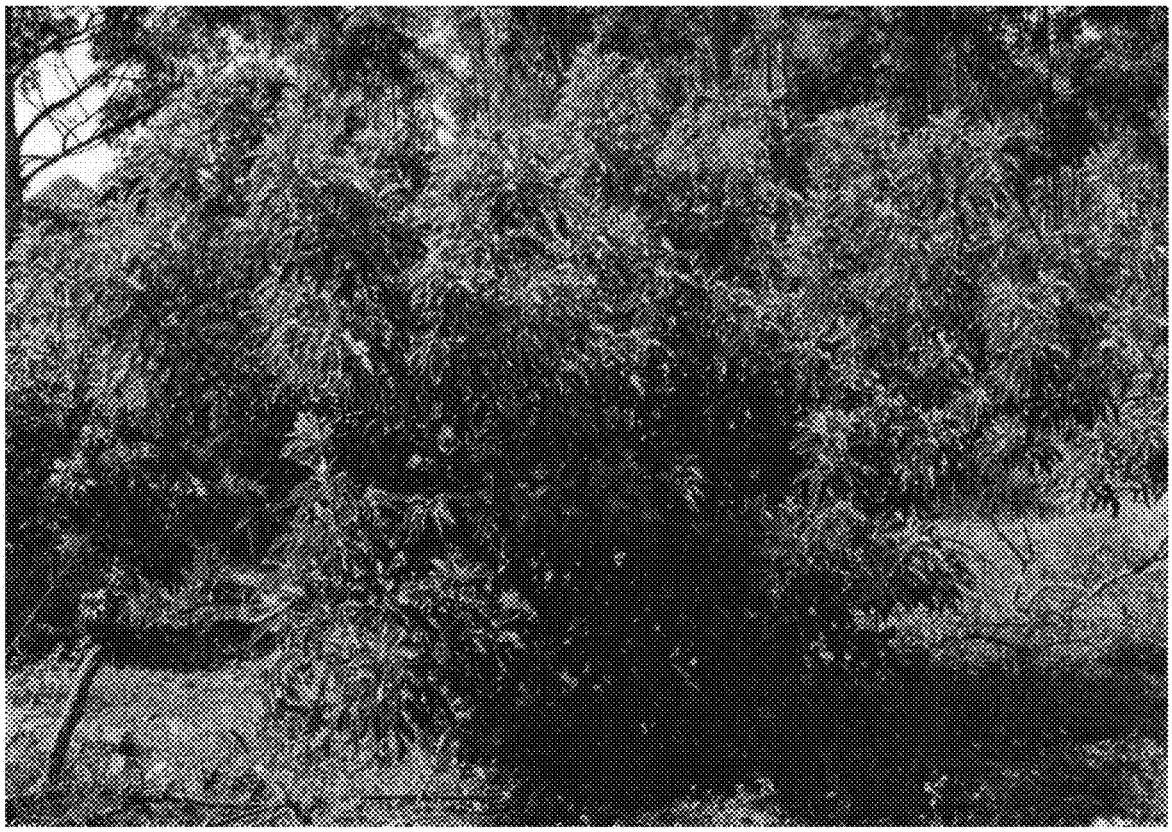
FIG. 1 is a photograph of a two-year-old, top-worked tree of the 'Merensky 5' variety on 'Merensky 2' rootstock, growing in Tzaneen, Limpopo Province, South Africa.

With reference to FIG. 1, the growth habit of the 'Merensky 5' variety is spreading. Table 1 below is data on the vigor of the 'Hass' grafted onto the rootstock of the 'Merensky 5' as determined by trunk diameter measurements, taken 5 cm above the soil line, from trees planted in an orchard with negligible *Phytophthora cinnamomi* and salinity levels in Goleta, Calif., USA.

TABLE 1

| | Trunk diameter (cm) | | |
|---|---|---|---|
| Rootstock | Year 2 | Year 3 | Year 4 |
| 'Merensky 5' | 5.39 | 8.37 | 9.74 |
| 'Merensky 2' | 4.15 | 8.37 | 9.09 |

Goleta, California, USA, with 'Hass' scion (n = 15)

Below in Table 2 are data of the vigor of the 'Hass' grafted onto the rootstock of 'Merensky 5' as determined by trunk diameter measurements, taken 20 cm above the soil line, from trees planted in an orchard with *Phytophthora cinnamomi* and no salt in Tzaneen, Limpopo Province, South Africa.

TABLE 2

| | Trunk diameter (cm) | | |
|---|---|---|---|
| Rootstock | Year 2 | Year 3 | Year 4 |
| 'Merensky 5' | 2.67 | 3.21 | 3.94 |
| 'Merensky 2' | 3.13 | 3.91 | 5.19 |

Tzaneen, Limpopo Province, South Africa, with 'Hass' scion (n = 30)

Table 3 below illustrates the data on the typical canopy size of 'Hass' grafted onto the rootstock of 'Merensky 5' as determined by canopy volume measurements from trees planted in an orchard with negligible *Phytophthora cinnamomi* and salinity levels (Goleta, Calif., USA).

TABLE 3

| | Canopy volume ($m^3$) | | |
|---|---|---|---|
| Rootstock | Year 2 | Year 3 | Year 4 |
| 'Merensky 5' | 0.45 | 0.68 | 0.76 |
| 'Merensky 2' | 0.38 | 0.61 | 0.68 |

Goleta, California, USA, with 'Hass' scion (n = 15)

Table 4 below, for comparison, is data on the typical canopy size of 'Hass' grafted onto the rootstock of 'Merensky 5' as determined by canopy volume measurements from trees in an orchard with *Phytophthora cinnamomi* and no salt (Tzaneen, Limpopo Province, South Africa).

TABLE 4

| | Canopy volume ($m^3$) | |
|---|---|---|
| Rootstock | Year 3 | Year 4 |
| 'Merensky 5' | 0.29 | 0.34 |
| 'Merensky 2' | 0.33 | 0.42 |

Tzaneen, Limpopo Province, South Africa, with 'Hass' scion (n = 30)

Figure 2:
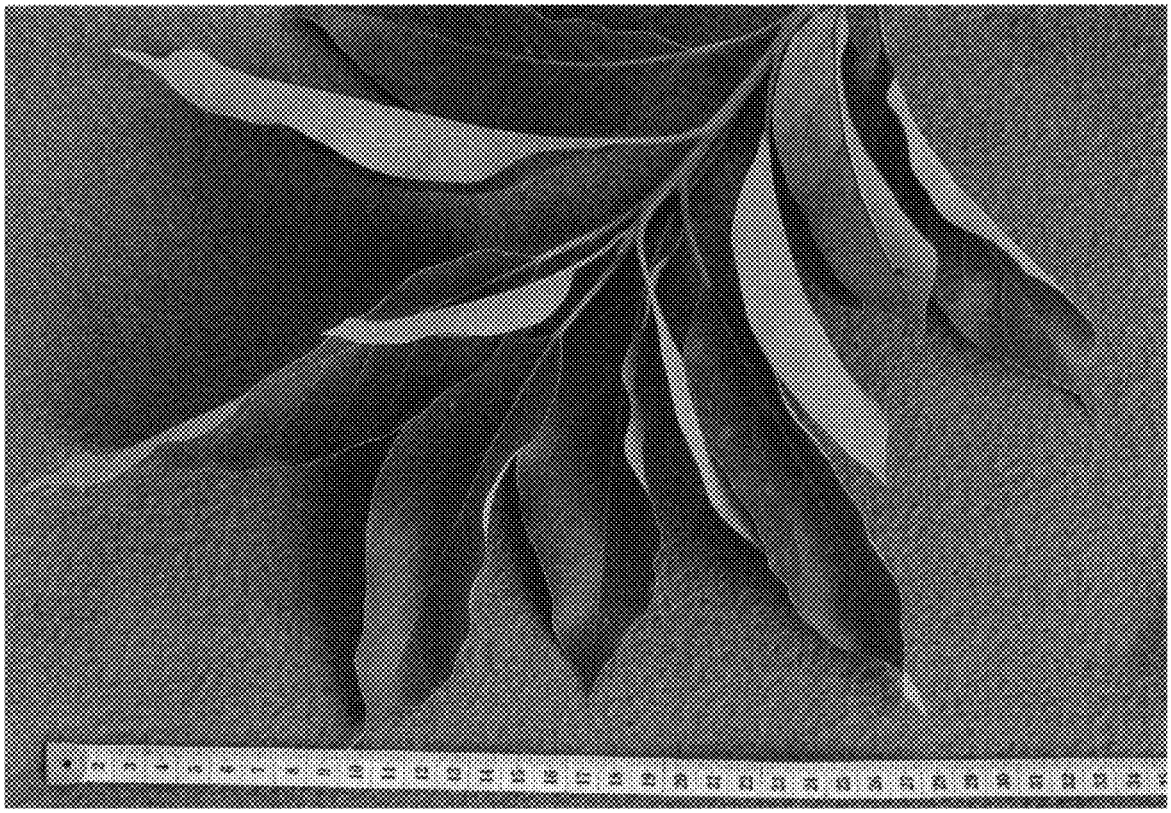
FIG. 2 is a photograph depicting typical mature foliage of the 'Merensky 5' variety, with a ruler, in centimeters, below for size reference.
Figure 3:
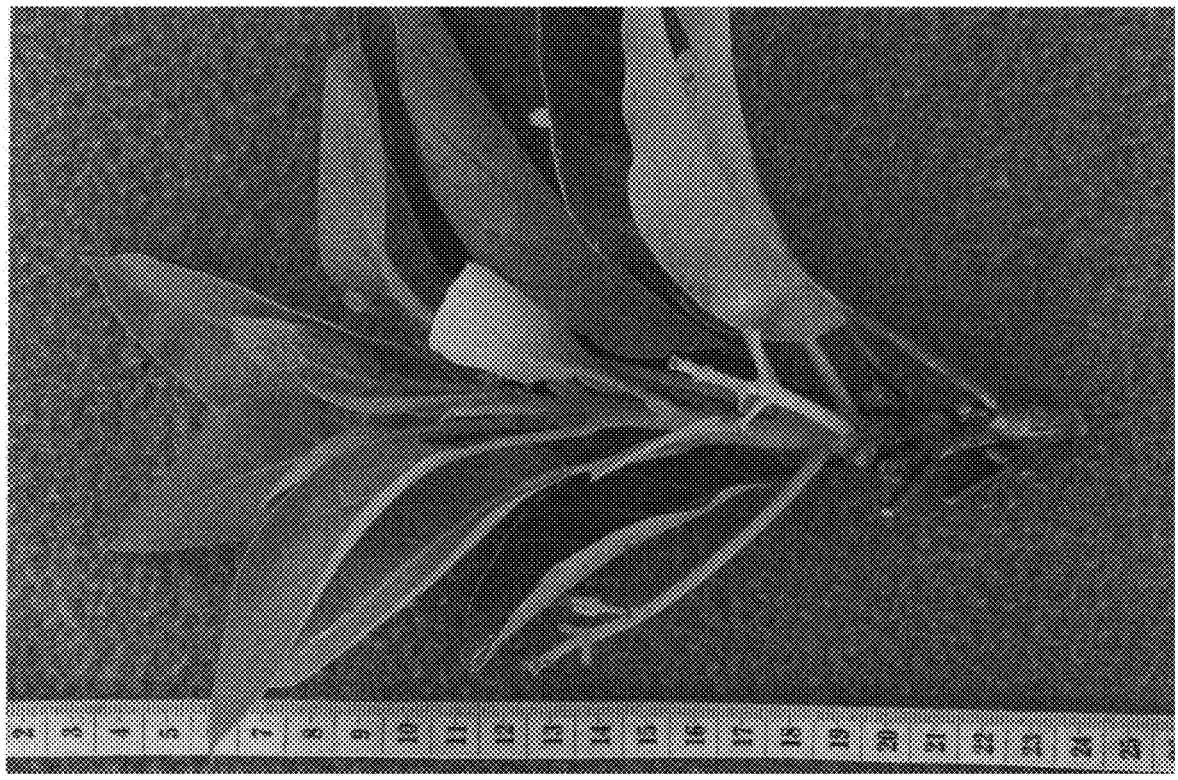
FIG. 3 is a photograph depicting typical flush foliage of the 'Merensky 5' variety, with size reference ruler below.
Figure 4:
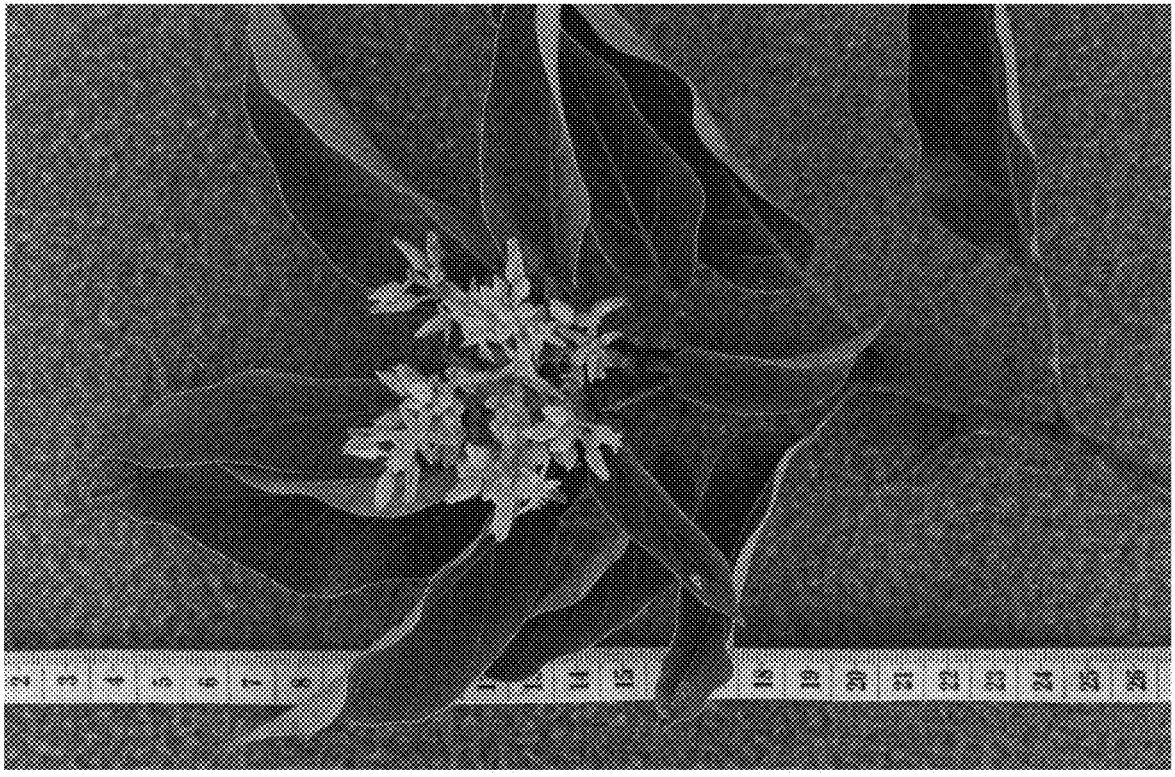
FIG. 4 is a photograph depicting typical inflorescence of the 'Merensky 5' variety, with a ruler below for size reference.

With reference to FIGS. 2-4, the color of a one-year-old branch is yellow-green (RHS 144A). The bark of the one-year-old branch is smooth. The lenticels of the one-year old branch are inconspicuous.

The main stem is grey-brown (RHS 199C). The texture of the bark of the main stem is corky.

The young shoot (flush) of the 'Merensky 5' has a medium intensity of anthocyanin coloration. The color of the flush is greyed-orange (RHS 165A). The conspicuousness of the lenticels is high. The lenticels are greyed-purple (RHS 85B). By comparison, lenticels in 'Duke 7' are green (RHS 139B). The lenticels are approximately 1.0 mm long. The lenticels have a concentration of +/−15 lenticels per square cm. The upper side of the young leaves is a yellow-green (RHS 152A) color. The upper side of the young leaves has a high glossiness. The color of the lower surface of the young leaves is grey-brown (RHS 199A).

A mature leaf has a length of approximately 15.3 cm and a width of approximately 6.3 cm. This provides a ratio of 2.4 length/width. The shape of the mature leaf is lanceolate. The color of the upper side of the mature leaf is yellow-green (RHS 147A). The upper side of the mature leaf has a medium glossiness. The color of the lower side of the mature leaf is green (RHS N138C). The veins on the lower side of the mature leaf are prominent and in relief. The color of the veins of the mature leaf are yellow-green (RHS 151A). The general shape and cross-section of a mature leaf is concave. Reflexing of apex in the mature leaf is present. The color of the petiole of the mature leaf is yellow-green (RHS 144B). The mature leaf has a medium anise aroma. The margin of the mature leaf has a medium undulation, and an acute leaf apex shape. The leaf base shape is acute. The length of the leaf petiole is approximately 3.7 cm. The leaves are held horizontally, i.e. approximately perpendicular to the shoot.

With particular reference to FIG. 4, the flower of the 'Merensky 5' will now be described. The flower has a bud size of approximately 5 mm in length and approximately 4 mm in diameter. The bud shape is ovoid. The bud color is yellow-green (RHS 145A). The flower belongs to Group "B", with the female opening occurring in the afternoon and the male opening the next morning. The flower's opening cycle lasts 20-24 hours. The petals are borne in two whorls of three perianth lobes. The petals possess entire margins and petal coloration is yellow-green (RHS 145C). There are commonly nine fertile stamens, with each having two basal orange nectar glands and three staminodia. The anthers are tetrathecal. The single pistil with a slender style and small stigmatic surface has one carpel with one ovule. The ovary is superior. The pedicel is commonly approximately 5 mm in length and approximately 1.5 mm in diameter. The coloration of the pedicel is yellow-green (RHS 145B). There are approximately 80-120 flowers per inflorescence. Generally, the 'Merensky 5' has been found to bloom in July-August at Tzaneen, Limpopo Province, South Africa. However, the flowering time in California, USA, is typically March-April.

Figure 5:
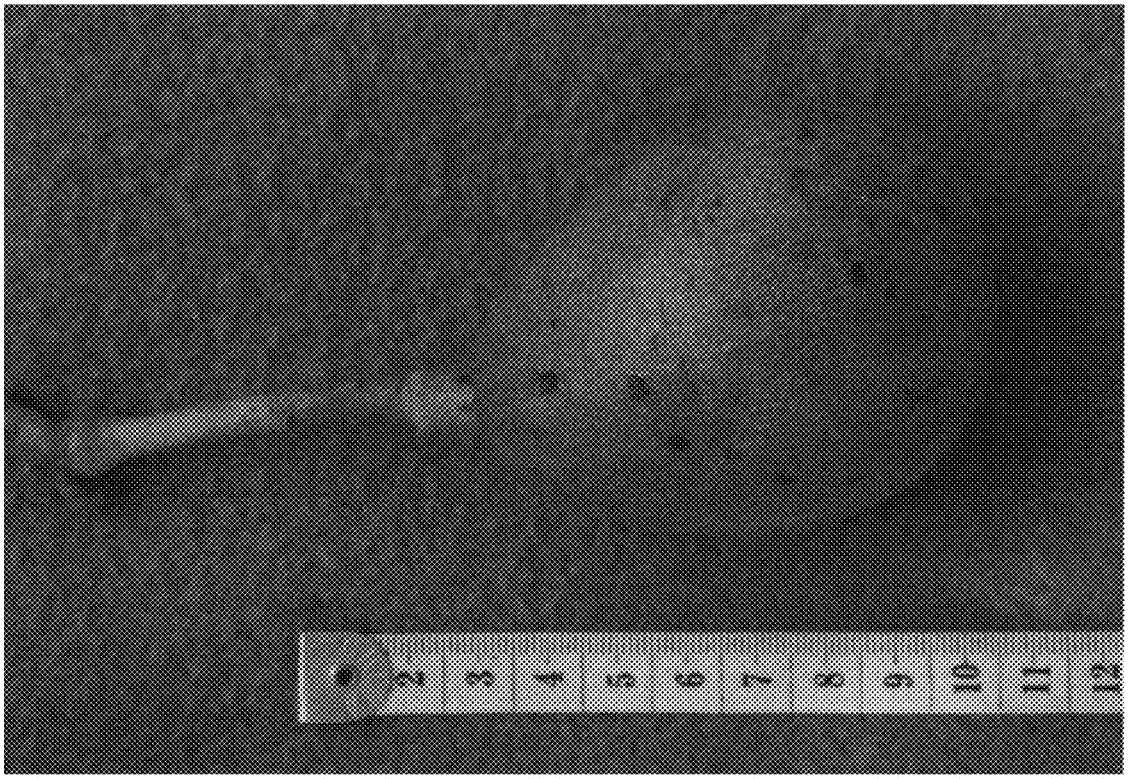
FIG. 5 is a photograph depicting a typical external view of the fruit of the 'Merensky 5' variety, adjacent a ruler for size comparison.
Figure 6:
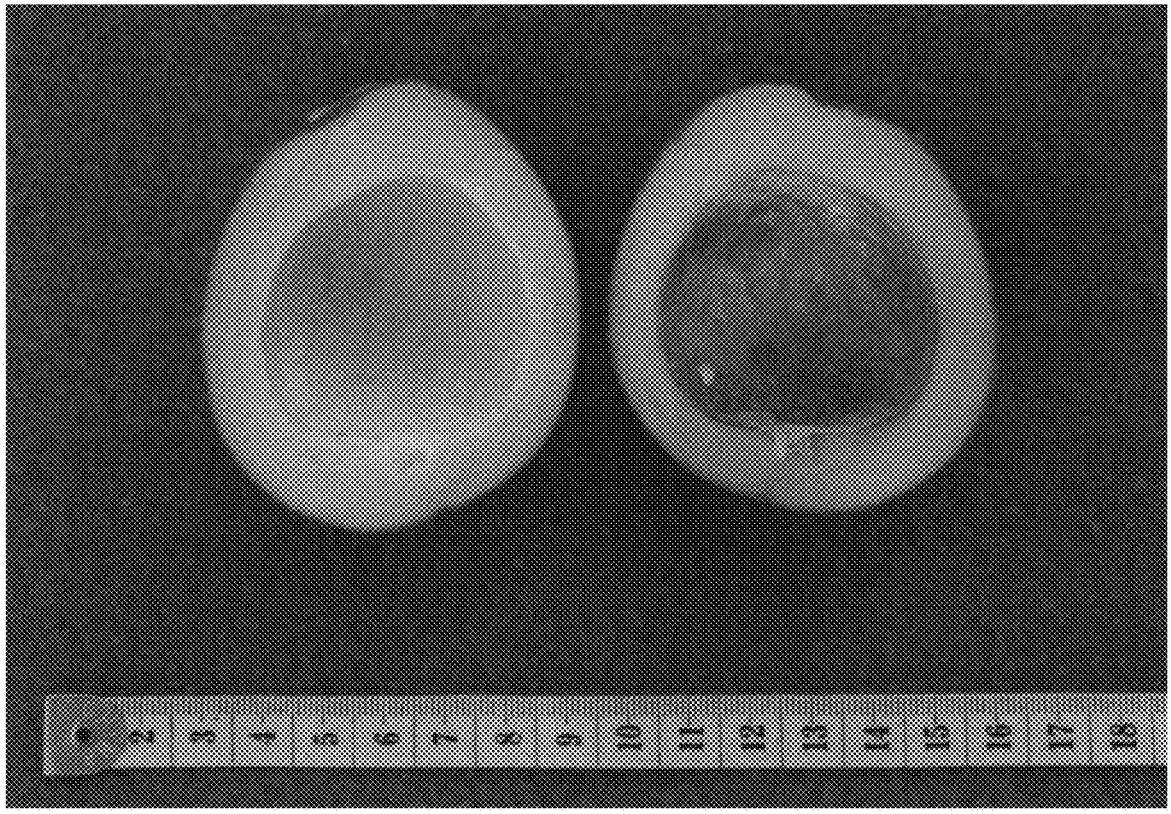
FIG. 6 is a photograph depicting internal views of the fruit of the 'Merensky 5' variety, with and without the seed, respectively, adjacent to a ruler for size reference.

With reference now to FIGS. 5 and 6, the fruit and seed of the 'Merensky 5' variety will now be described. The fruit is typically 7.0 cm in length and approximately 5.6 cm in width, providing a length/width ratio of 1.3. The shape of the fruit is obovate. The color of the skin of the fruit, when ripe, is yellow-green (RHS 146A). The skin texture is smooth. There are no longitudinal ridges. The skin is very thin. The skin adherence to the flesh is weak. The main color of the flesh is yellow-green (RHS 154D). The color of intensely colored area of flesh next to the skin is yellow-green (RHS 144A). The width of the intensely colored area of flesh next to the skin is approximately 1.0 mm. Fibers in the flesh are conspicuous.

The seed is approximately 4.1 cm in length and 3.8 cm in width in size. The seed has a generally triangular shape, in longitudinal section, and a generally circular shape in cross-section. The color of the seed coat, when fresh, is greyed-orange (RHS 165A).

The 'Merensky 5' fruit ripened in February in Tzaneen, South Africa and in October in California, USA. The fruit of the 'Merensky 5' is not intended for market use, but rather the variety is used as a rootstock onto which commercial varieties such as 'Hass' are grafted.

As can be seen from the data in Table 5 below, the 'Merensky 5' rootstock having 'Hass' scion yielded a greater cumulative yield in kilograms per tree than a 'Merensky 2' rootstock having the 'Hass' scion.

TABLE 5

| | Yield (kg/tree) | | | |
|---|---|---|---|---|
| Rootstock | Year 2 | Year 3 | Year 4 | Cumulative |
| 'Merensky 5' | 7.22 | 13.72 | 58.01 | 78.95 |
| 'Merensky 2' | 11.03 | 14.03 | 43.19 | 68.25 |

Tzaneen, Limpopo Province, South Africa, with Hass scion

The 'Merensky 5' variety has shown a strong resistance and tolerance to *Phytophthora cinnamomi*. Moreover, 'Merensky 5' has shown to be tolerant to salinity.

What is claimed is:

1. A new and distinct rootstock variety of avocado tree having the characteristics as described and illustrated herein.

* * * * *